(12) United States Patent
Osaki et al.

(10) Patent No.: US 6,675,352 B1
(45) Date of Patent: Jan. 6, 2004

(54) METHOD OF AND APPARATUS FOR EDITING ANNOTATION COMMAND DATA

(75) Inventors: Takanobu Osaki, Hachioji (JP); Hideyuki Ban, Hachioji (JP); Hitoshi Matsuo, Musashino (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/320,557

(22) Filed: May 27, 1999

(30) Foreign Application Priority Data

May 29, 1998 (JP) .......................................... 10-148716

(51) Int. Cl.$^7$ ........................ G06F 15/00; G06F 17/00; G09G 5/00
(52) U.S. Cl. ..................... 715/512; 715/500.1; 345/723; 345/725; 345/726
(58) Field of Search ........................... 707/500.01, 512, 707/537; 345/724, 725, 726, 723; 715/500.1, 537, 512

(56) References Cited

U.S. PATENT DOCUMENTS

| | | | | |
|---|---|---|---|---|
| 5,440,678 A | * | 8/1995 | Eisen et al. .................. | 345/723 |
| 5,535,063 A | * | 7/1996 | Lamming ..................... | 360/4 |
| 5,583,980 A | * | 12/1996 | Anderson .................... | 345/473 |
| 5,600,775 A | * | 2/1997 | King et al. .................. | 707/500 |
| 5,768,607 A | * | 6/1998 | Drews et al. ............. | 707/500.1 |
| 5,920,317 A | * | 7/1999 | McDonald .................. | 345/835 |
| 6,105,055 A | * | 8/2000 | Pizano et al. .......... | 340/825.01 |
| 6,178,431 B1 | * | 1/2001 | Douglas ...................... | 707/512 |
| 6,230,172 B1 | * | 5/2001 | Purnaveja et al. .......... | 707/500 |
| 6,332,147 B1 | * | 12/2001 | Moran et al. ............ | 707/500.1 |

OTHER PUBLICATIONS

Chong, M.N. et al., "Concurrent processing for picture archiving and communication system (PACS)", Jul. 3–7, 1995, Proceedings of IEEE Singapore International Conference, Theme: Electrotechnology 2000: Communications and Networks, pp. 468–472.*

Kilman et al., "An International Collaboratory based on Virtual Patient Records", Aug. 1997, Communications of the ACM, vol. 40, No. 8, pp. 111–117.*

Chin–Hwa Kuo et al., "A synchronization scheme for mulitmedia annotation", Oct. 12–15, 1997, IEEE International Conference: Systems, Man, and Cybernetics, vol. 1, pp. 594–598.*

Wilcox, L. et al., "Annotation and segmentation for multimedia indexing and retrieval", Jan. 6–9, 1998, Proceedings of the Thirty–First International Conference on System Sciences, vol. 2, pp. 259–266.*

"Computer Assisted Radiography" 1996—pp. 417–420.

Proc. SPIE, vol. 2165, pp. 9–20 (1994).

* cited by examiner

*Primary Examiner*—Joseph H. Feild
*Assistant Examiner*—Almari Romero

(57) ABSTRACT

An annotation command data for annotating a displayed image is in the form of an original data block having a first data area holding an initial state for the displayed image and a second data area holding one or more commands and a starting time point of execution for each of the commands. Execution of each command is started at its associated starting time point of execution. For editing of the annotation command data, the original data block may be divided to produce therefrom plural secondary data blocks each having an initial state, a part of the one or more commands and a starting time point of execution for each of the part of the commands, so that one of the secondary data blocks is deleted, or a new data block having an initial state, one or more commands and starting time point of execution therefor is inserted between the secondary data blocks.

3 Claims, 13 Drawing Sheets

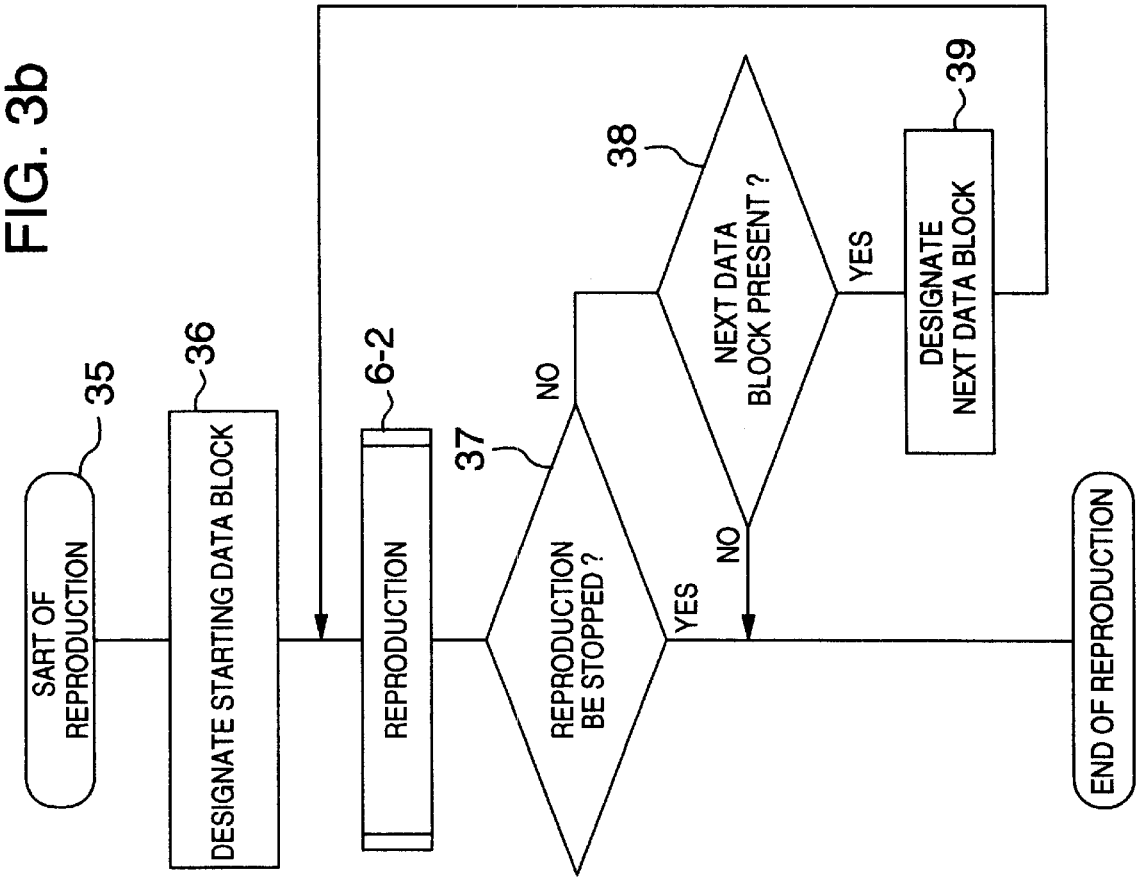
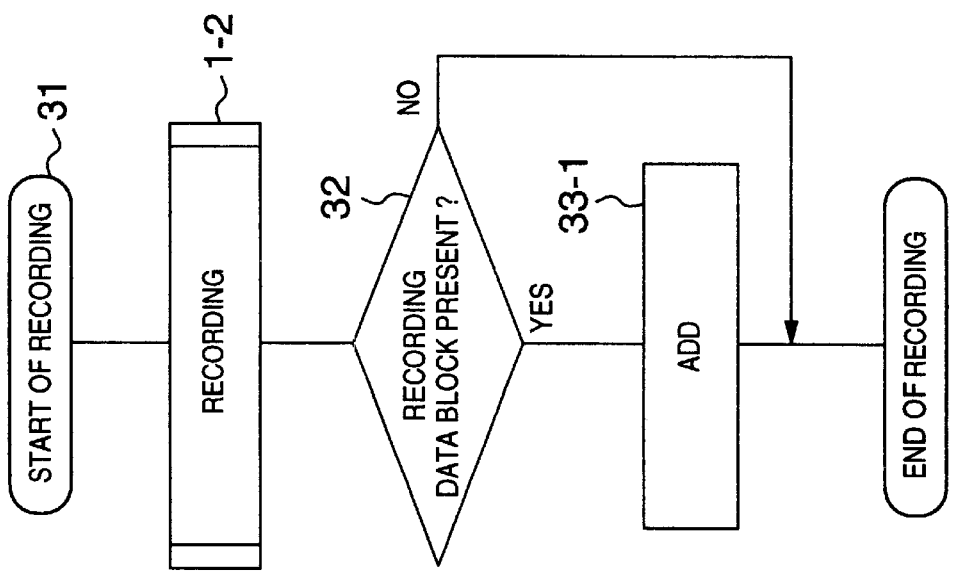

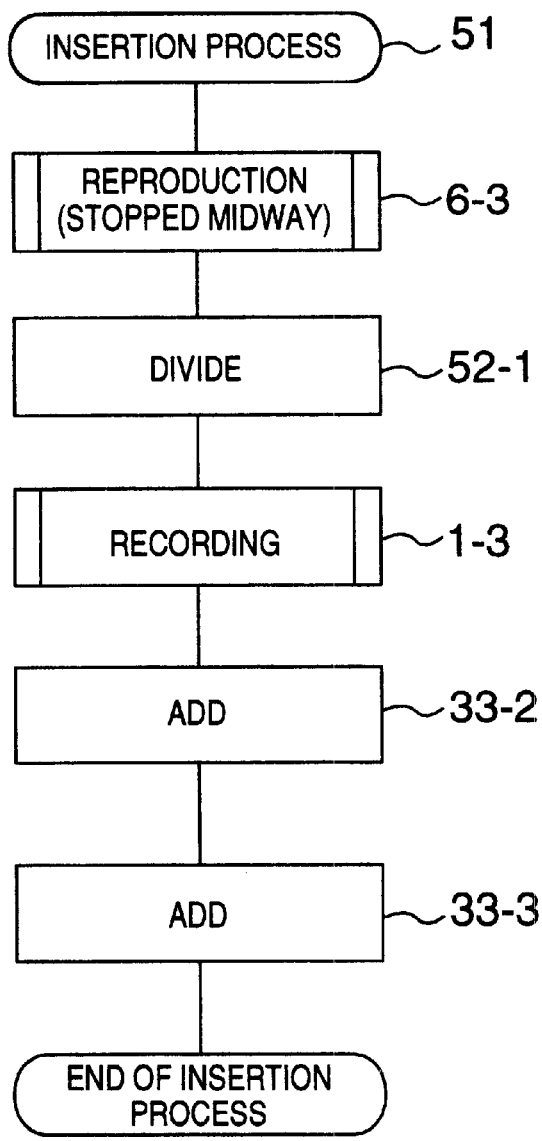
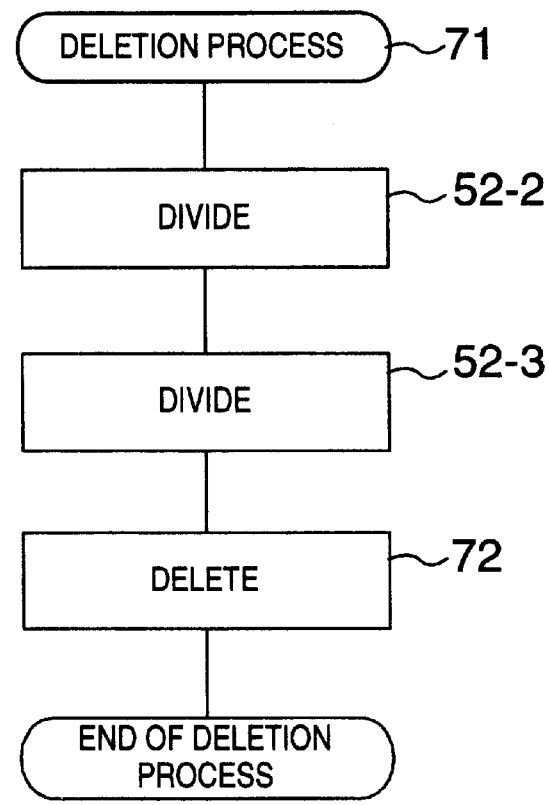

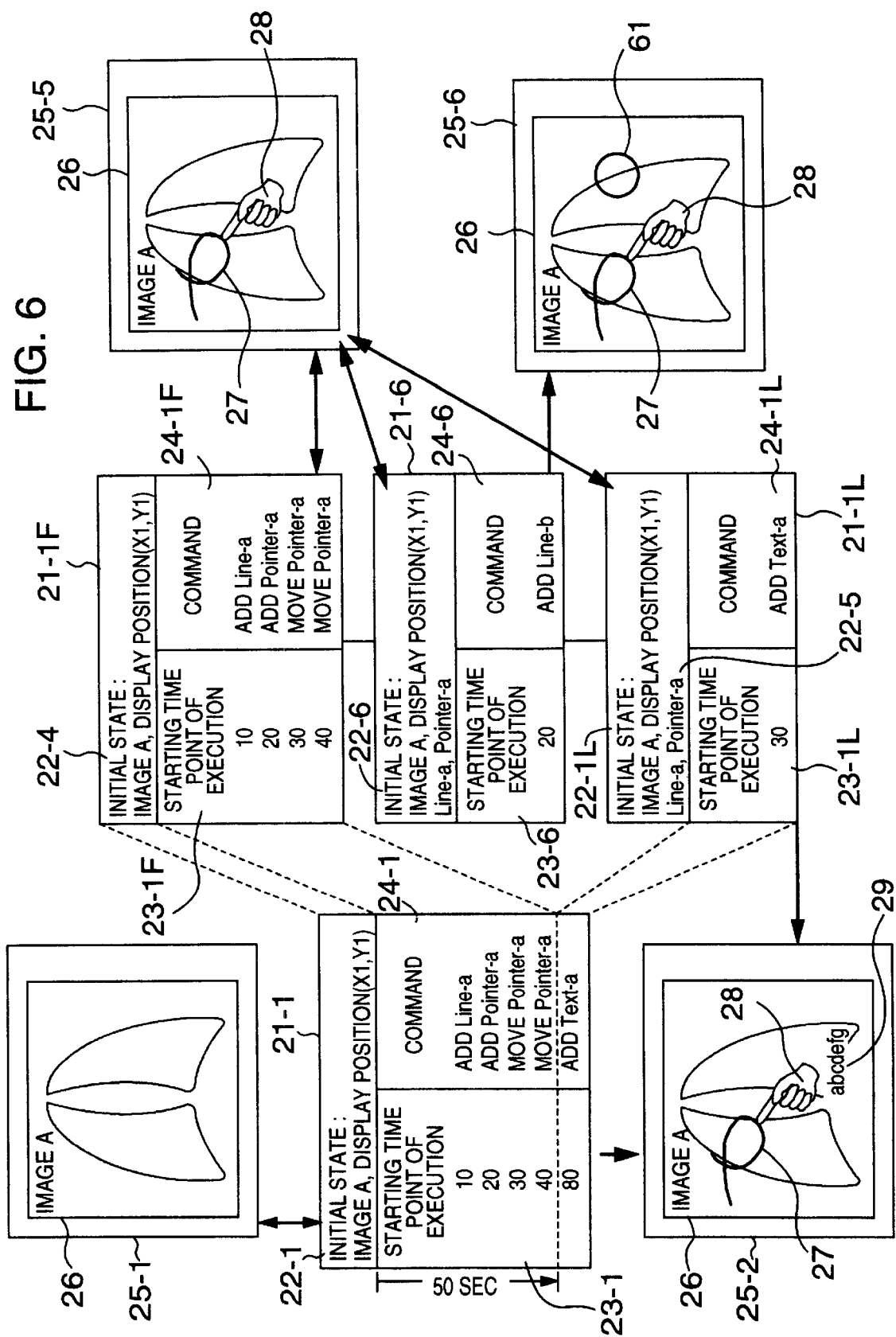

| GENERATION INFORMATION : 1 | | |
|---|---|---|
| INITIAL STATE : IMAGE A, DISPLAY POSITION(X1,Y1) | | |
| STARTING TIME POINT OF EXECUTION | COMMAND | SOUND DATA |
| 10 | ADD Line-a | |
| 20 | ADD Pointer-a | |
| 30 | MOVE Pointer-a | |
| 40 | MOVE Pointer-a | |

| GENERATION INFORMATION : 1 | | |
|---|---|---|
| INITIAL STATE : IMAGE A, DISPLAY POSITION(X1,Y1) | | |
| STARTING TIME POINT OF EXECUTION | COMMAND | MOTION PICTURE DATA |
| 10 | ADD Line-a | |
| 20 | ADD Pointer-a | |
| 30 | MOVE Pointer-a | |
| 40 | MOVE Pointer-a | |

| GENERATION INFORMATION : 1 | | | |
|---|---|---|---|
| INITIAL STATE : IMAGE A, DISPLAY POSITION(X1,Y1) | | | |
| STARTING TIME POINT OF EXECUTION | COMMAND | SOUND DATA | MOTION PICTURE DATA |
| 10 | ADD Line-a | | |
| 20 | ADD Pointer-a | | |
| 30 | MOVE Pointer-a | | |
| 40 | MOVE Pointer-a | | |

114-2, 115-2

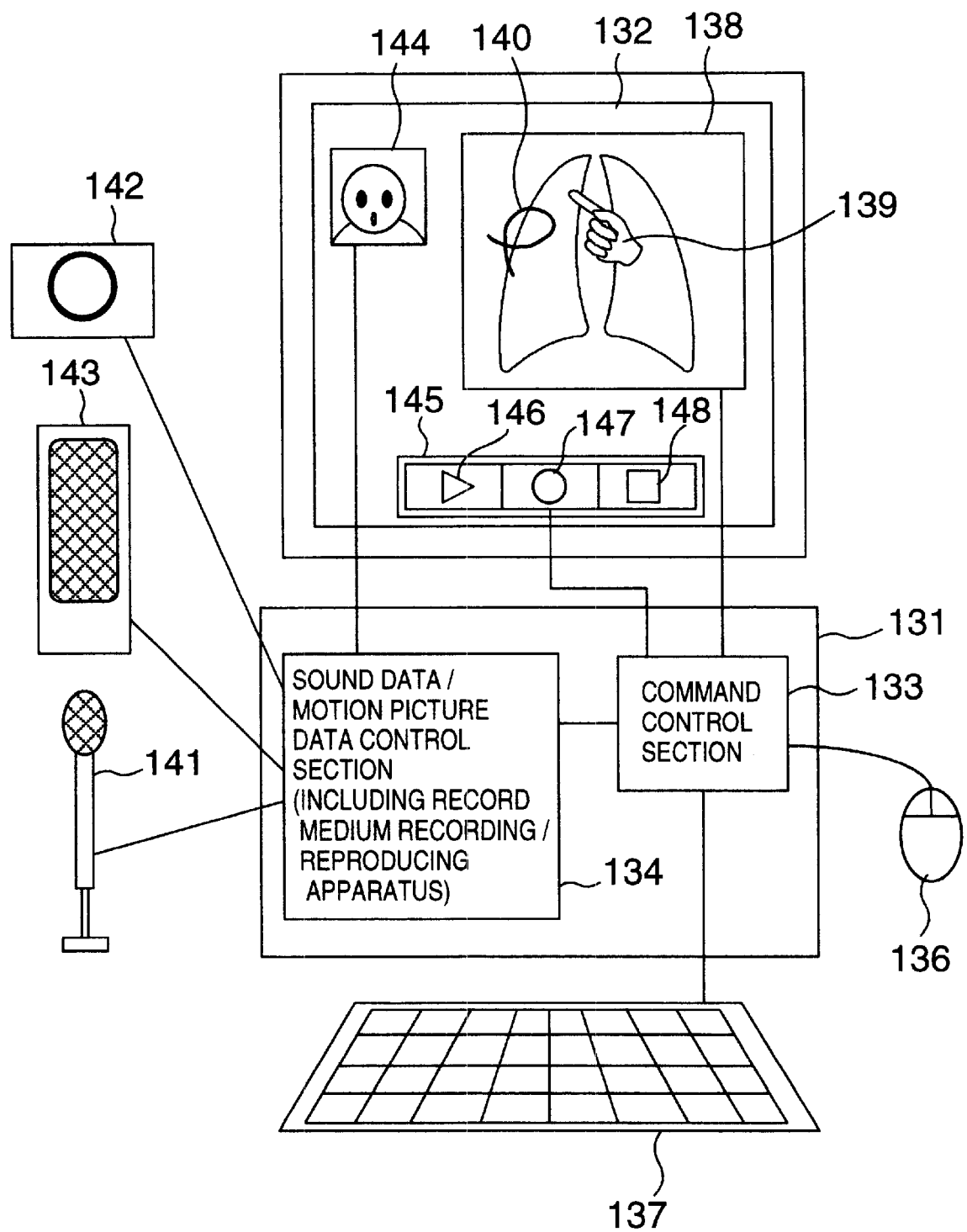

| GENERATION INFORMATION : 1 | | |
|---|---|---|
| F1 | | |
| C1 | S1 | M1 |

151-2

| GENERATION INFORMATION : 2 | | |
|---|---|---|
| F3 | | |
| C3 | S3 | M3 |

151-3

| GENERATION INFORMATION : 1 | | |
|---|---|---|
| F2 | | |
| C2 | S2 | M2 |

| | | |
|---|---|---|
| F1 | INITIAL STATE :<br>IMAGE A, DISPLAY POSITION(X1,Y1) | |
| C1 | STARTING TIME POINT OF EXECUTION<br>10<br>20<br>30 | COMMAND<br>ADD Line-a<br>ADD Pointer-a<br>MOVE Pointer-a |
| C2 | 40 | MOVE Pointer-a |
| S1 | SOUND DATA | |
| S2 | | |
| M1 | MOTION PICTURE DATA | |
| M2 | | |
| F2 | INITIAL STATE :<br>IMAGE A, DISPLAY POSITION(X1,Y1)<br>Line-a, Pointer-a | |
| F3 | INITIAL STATE :<br>IMAGE A, DISPLAY POSITION(X1,Y1)<br>Line-a, Pointer-a | |
| M3 | MOTION PICTURE DATA | |
| C3 | STARTING TIME POINT OF EXECUTION<br>20 | COMMAND<br>ADD Line-b |
| S3 | SOUND DATA | |

METHOD OF AND APPARATUS FOR EDITING ANNOTATION COMMAND DATA

BACKGROUND OF THE INVENTION

The present invention relates to a method of editing annotation command data, an apparatus using this method, and a medium for storing data recorded by this method.

For handling multimedia data that needs to be processed by a computer, a system has been known which records voice and operations performed by a user and the result of operations and which plays back the recorded voice and operations in synchronization with each other. For example, a system is available which displays a medical image on a computer screen and records/replays annotations and voiced observations made by a doctor concerning the image during a remote consultation session. A system capable of transferring recorded observations of one doctor to another doctor has been reported (Computer Assisted Radiology, pp417–420 (1996)). For realizing such a system, a method is available which records or plays back voice in parallel with annotation. During recording, voice is recorded as continuous data and annotation command data and command execution timings are also recorded. During playback, the recorded voice is played back and at the same time the recorded annotation commands are executed in synchronization with the annotation timings. The voice and annotations can be synchronously recorded or played back by simultaneously starting their recording or playback.

In recording such commands along with the elapse of time, there may be a case where some commands are executed in advance to prepare for the recording. For example, an image to be referenced is displayed and undergoes some processing, such as enlargement, for ease of viewing before actually starting the recording. The processing performed prior to the start of recording may be stored in the form of commands so that it can be reproduced. These commands may, however, include redundant processing. For example, when the image is enlarged and then reduced, the enlargement is canceled by the reduction and therefore storing both enlargement and reduction steps is redundant. This problem is not addressed by conventional technologies. Further, when queries and answers are transmitted and received using multimedia data, the answers can be created as if the parties concerned are engaged in conversation, as by quoting the received query in his or her reply. To realize this requires editing such as insertion of command data into other command data. However, changing the sequence of command data for the editing may cause a problem that the final result (the image displayed at the end of the execution) of the edited command data is different from the final result of the original command data which is not edited.

SUMMARY OF THE INVENTION

An object of the present invention is to provide a method of preparing an easily editable annotation command data.

Another object of the present invention is to provide a method of editing an annotation command data, carried on a medium, for annotating a to-be-annotated image.

Another object of the present invention is to provide a medium storing an annotation command data in the form of a data block including an initial state, a series of annotating commands and a starting time point of execution for each of the annotating commands.

Other objects and advantages of the present invention will be apparent from the following description of embodiments of the present invention made with reference to the accompanying drawings.

Term "annotation" used in the present invention is intended to mean various operations or manipulation results thereof such as display of a to-be-annotated image itself, termination of display of an image, addition of a pointer indicating a particular portion (such as a region of interest) of a to-be-annotated image on a display screen, movement of the pointer on the display screen, addition of a line (lines) and/or a character (characters) on the display screen on which a to-be-annotated image is displayed, and also changes of a display state of an image on the display screen (such as enlargement/reduction, a change of reproduction tone (brightness, contrast, color table) and/or filtering), which may be necessary to annotate a to-be-annotated image.

According to one aspect of the present invention, an annotation command data is prepared as follows: namely, an initial state for a to-be-annotated image is recorded on a first record area of a record medium, and then at least one command and a starting time point of execution for each of the at least one command are recorded on a second record area of the record medium, in which execution of the command is started at its associated starting time point of execution, the command being for annotating said to-be-annotated image, and the first and second record areas being associated in their location with each other to form a data block.

According to another aspect of the present invention, an annotation command data for annotating a displayed image is in the form of an original data block having a first data area holding an initial state for the displayed image and a second data area holding one or more commands and a starting time point of execution for each of the commands. Execution of each command is started at its associated starting time point of execution. For editing of the annotation command data, the original data block may be divided to produce therefrom plural secondary data blocks each having an initial state, a part of the one or more commands and a starting time point of execution for each of the part of the commands, so that one of the secondary data blocks is deleted, or a new data block having an initial state, one or more commands and staring time point of execution therefor is inserted between the secondary data blocks.

BRIEF DESCRIPTION OF THE DRAWINGS

FIGS. 3a and 3b are flow charts showing methods of recording and reproducing annotation command data having a plurality of data blocks, according to one embodiment of the invention;

FIG. 5 is a flow chart showing an annotation command data editing method for inserting a new data block, according to one embodiment of the invention;

FIG. 6 illustrates how a data block structure changes when a data block is inserted by using the method of FIG. 5, and also illustrates screens showing images associated with some data blocks;

FIG. 7 is a flow chart showing an annotation command data editing method for deleting an intermediate part of the data block, according to one embodiment of the invention;

FIGS. 12a, 12b and 12c illustrate data block structures in which sound data, motion picture data and annotation command data are combined, according to one embodiment of the invention;

FIG. 13 is a schematic view showing a system that supports medical examination by using multimedia data blocks containing a combination of sound data, motion picture data and annotation command data attached with starting time points of execution, according to one embodiment of the invention; and FIGS. 14a and 14b illustrate example data blocks recorded in a recording medium, and example pointers indicating recorded positions of the data blocks in data area.

DETAILED DESCRIPTION OF THE INVENTION

In embodiments described below, we will explain about an example case where queries and answers are recorded and reproduced while manipulating an image displayed on a computer screen. With an image to be displayed on the computer screen taken as an object to be annotated, commands are used to perform image annotating operations, such as display of a to-be-annotated image itself, termination of display of an image, addition of a pointer indicating a particular portion of a to-be-annotated image on a display screen, movement of the pointer on the display screen, addition of a line (lines)/a character (characters) on the display screen on which a to-be-annotated image is displayed, changes of a display state of an image on the display screen (such as enlargement/reduction, a change of reproduction tone and/or filtering).

Figure 1A:
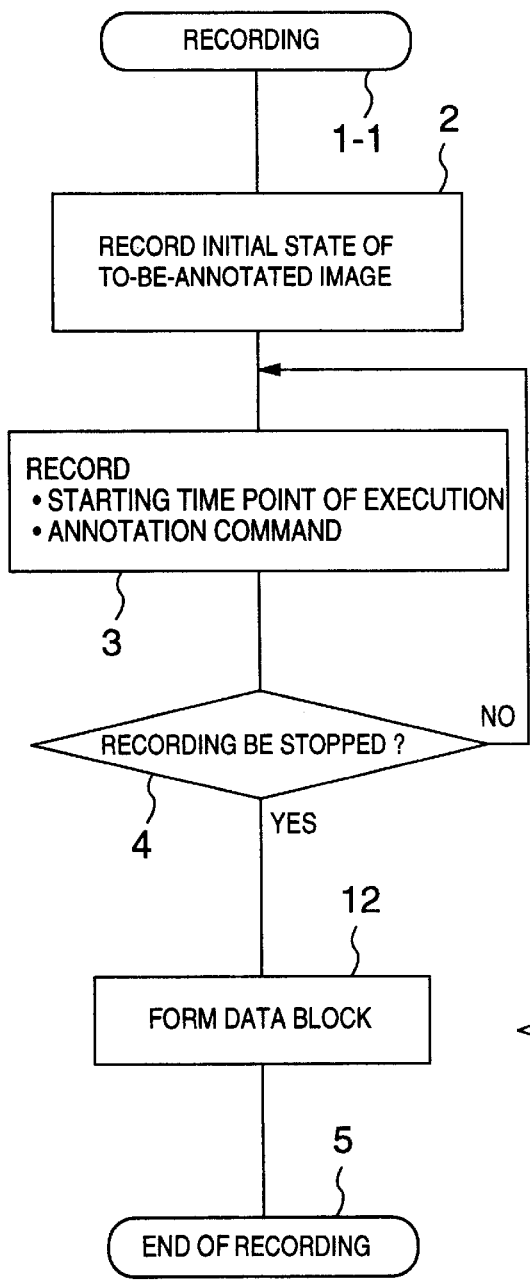
FIGS. 1a and 1b are flow charts showing annotation command data recording and reproducing methods according to one embodiment of the present invention.
Figure 1B:
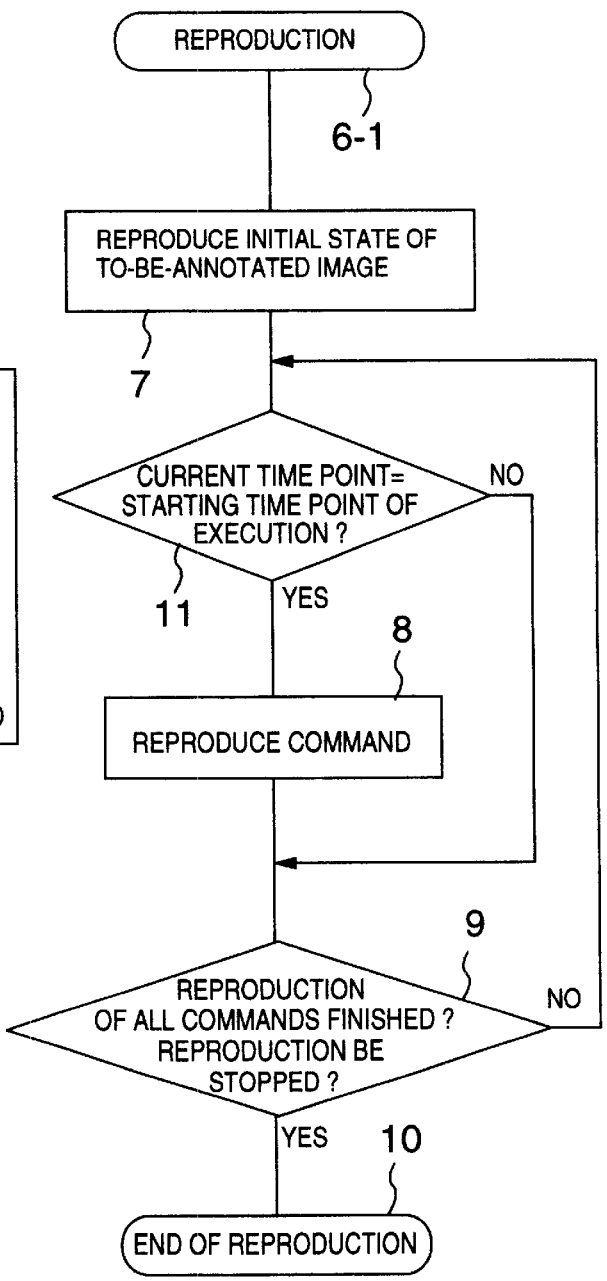

FIGS. 1a and 1b are flow charts representing example processes for recording and reproducing annotation command data (data block) according to one embodiment of the present invention. A recording process 1-1 shown in FIG. 1a first performs an initial state recording step 2 to record an initial state of a to-be-annotated image and then a starting time point of execution/command recording step 3 to record starting time points of command execution and commands. Until the recording is stopped (step 4), the starting time point of execution/command recording step 3 is repeated and the recorded initial state, starting time points of execution and command data are combined to generate a data block, after which the recording is terminated (step 5). A reproduction process 6-1 first performs an initial state reproducing step 7 to reproduce the initial state of the annotated image. With the initial state completely reproduced, when the time that has elapsed from the start of command data reproduction coincides with the starting time point of execution (step 11), the corresponding command is executed at a command reproducing step 8. The command reproducing step 8 is repeated until all commands are executed (step 9) or the reproduction is stopped (step 9), at which time the reproduction is ended (step 10).

Figure 2:
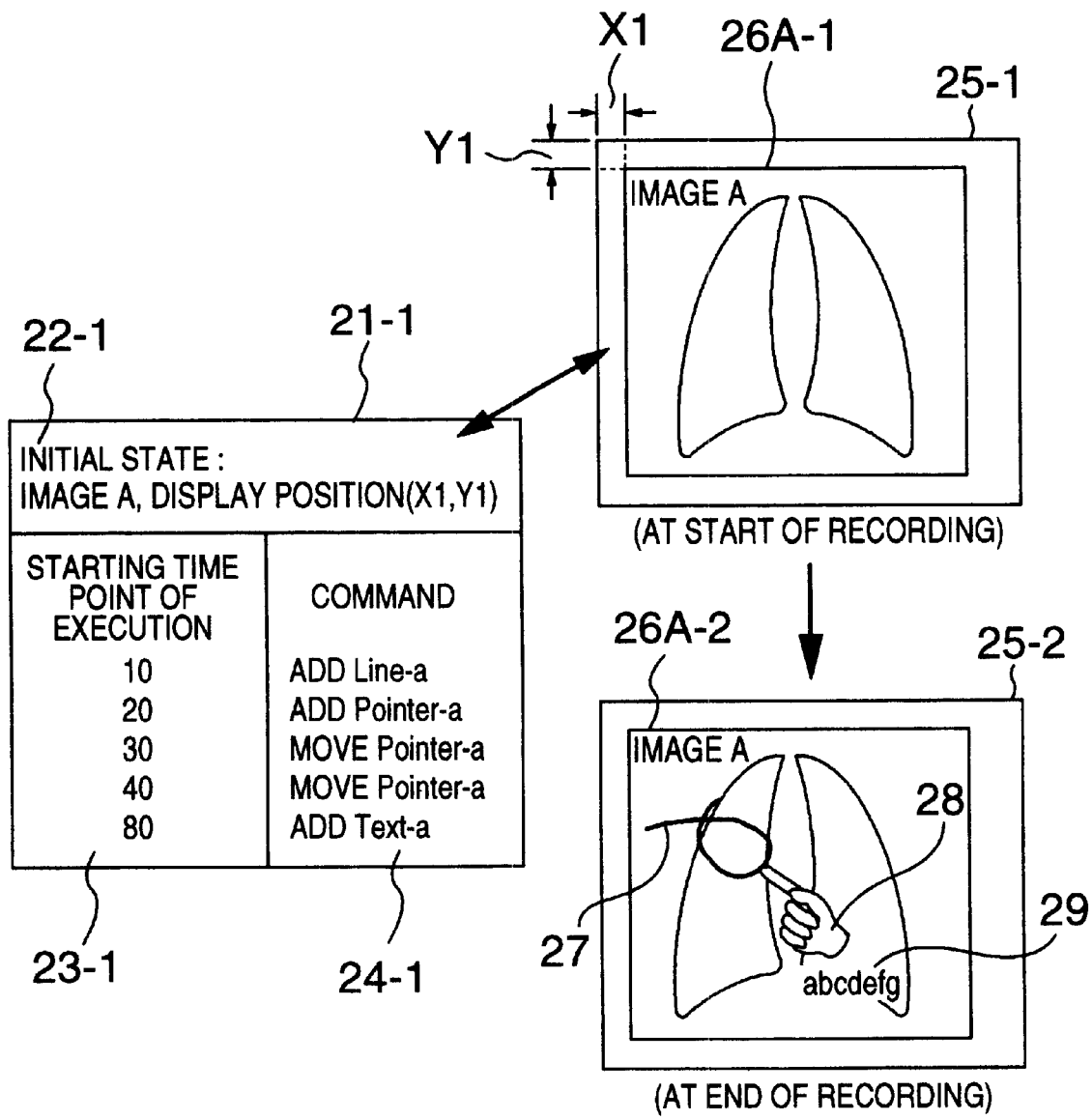
FIG. 2 illustrates a data block structure and a screen showing an example of a to-be-annotated image and a screen showing an example of an annotated image according to one embodiment of the invention.

FIG. 2 shows the structure of a data block, including command data with starting time points of execution (hereafter, referred to as execution start times for simplicity), which is recorded according to the flow chart of FIG. 1a. FIG. 2 also shows example images displayed. A recorded data block 21-1 has an initial state 22-1 of a to-be-annotated image, command execution start times 23-1 (which in this case represent the times in seconds that have elapsed from the start of recording), and commands (of which there could be only one) 24-1. When the recording is started, a to-be-annotated image A (26A-1) is displayed on the computer screen 25-1. When the recording is finished, the computer screen 25-2 shows a line-a (27), a pointer-a (28) and a text-a (29) added to the image A.

Before starting the recording, an operator displays some images retrieved from database and looks for a desired one. When the desired image A is found, other images are closed and the image 26A-1 (image A) is redisplayed with its upper left corner positioned at coordinates (X1, Y1). Then, the operator enlarges the image A to view it and then restores the image A to its original size. The operator starts recording and annotating this image (for example, asking questions about the image). With the recording started, the recording process 1-1 records the state of the screen 25-1 present at the start of the recording, i.e., the initial state 22-1 of the image, into a recording medium at an initial state recording step 2. At this time, only the current state of the image A (26A-1) displayed at the coordinates (X1, Y1) is recorded, and annotations made prior to the start of the recording, such as display of other images for finding the image A, enlargement/reduction of the image A, are not included in the initial state 22-1. When the operator manipulates the image as by adding line-a (27) and pointer-a (28), moving the pointer twice, and adding text-a (29), the step 3 records execution start times 23-1 and commands 24-1 into the recording medium. The execution start time may, for example, be a period of time measured by a timer that has elapsed from the instant at which the recording of the initial state has been finished until the operation is executed. The recording area for the execution start times/commands is physically or logically related to the initial state recording area in terms of recording position, and these recording areas combine to form one data block.

Next, when the recorded data block 21-1 is reproduced, the reproduction process 6-1 reproduces the initial state 22-1 at the initial state reproducing step 7 to display the image A (26A-1) at the coordinates (X1, Y1) on the screen, thus producing a display 25-1. With the initial state reproduced, the command reproducing step 8 executes commands 24-1 at execution start times 23-1 (step 11) to reproduce the process of adding line-a (27) and pointer-a (28), moving the pointer twice and adding text-a (29) at the same timings as these operations were recorded. During the reproduction process, by initializing the timer when the initial state is completely reproduced and executing commands when the elapsed times of the timer reaches the execution start times, the results of execution of the commands can be reproduced at the same timings as they were executed during the recording. When the reproduction is finished, the computer screen 25-2 shows the same image 26A-2 that was displayed at the end of the recording.

In this embodiment, because the initial state that is present at the start of recording is first recorded before recording subsequent commands, only the state that has resulted from executing preceding commands prior to the start of recording is recorded as an initial state and the process of executing the preceding commands that has produced the initial state is not recorded. This enables optimum recording of annotation command data with no redundant processing (no redundant command execution). In the reproduction process, this can speed up the reproduction of the state that was present at the start of the recording and ensure accurate reproduction of a recorded session by executing only necessary commands.

Next, the process of recording and reproducing annotation command data containing a plurality of data blocks will be explained. FIGS. 3*a* and 3*b* show flow charts representing example processes of recording and reproducing a plurality of data blocks. In FIG. 3*a*, a recording step 1-2 records a data block in the same way as the recording step 1-2 of FIG. 1*a*. A check is made to see whether there is any recorded data block (step 32) and, if there is any, an addition step 33-1 adds the newly recorded data block to the existing data block, after which the process is terminated. When the step 32 decides that no recorded data block exists, the process is ended at this point. FIG. 3*b* shows a processing flow for reproducing a data block unit containing a plurality of data blocks. When the reproduction process is started (step 35), a starting data block is designated (step 36) and is reproduced at a reproduction step 6-2. The reproduction step 6-2 performs reproduction in the same way as does the reproduction step 6-1 of FIG. 1*b*. If the terminating condition (step 37) does not specify a reproduction halt and a decision step 38 decides that there is a next data block, the next data block is designated (step 39) and is then reproduced at the reproduction step 6-2. This reproduction process continues until the terminating condition 37 specifies the reproduction halt or all the data blocks have been reproduced (step 38).

Figure 4:
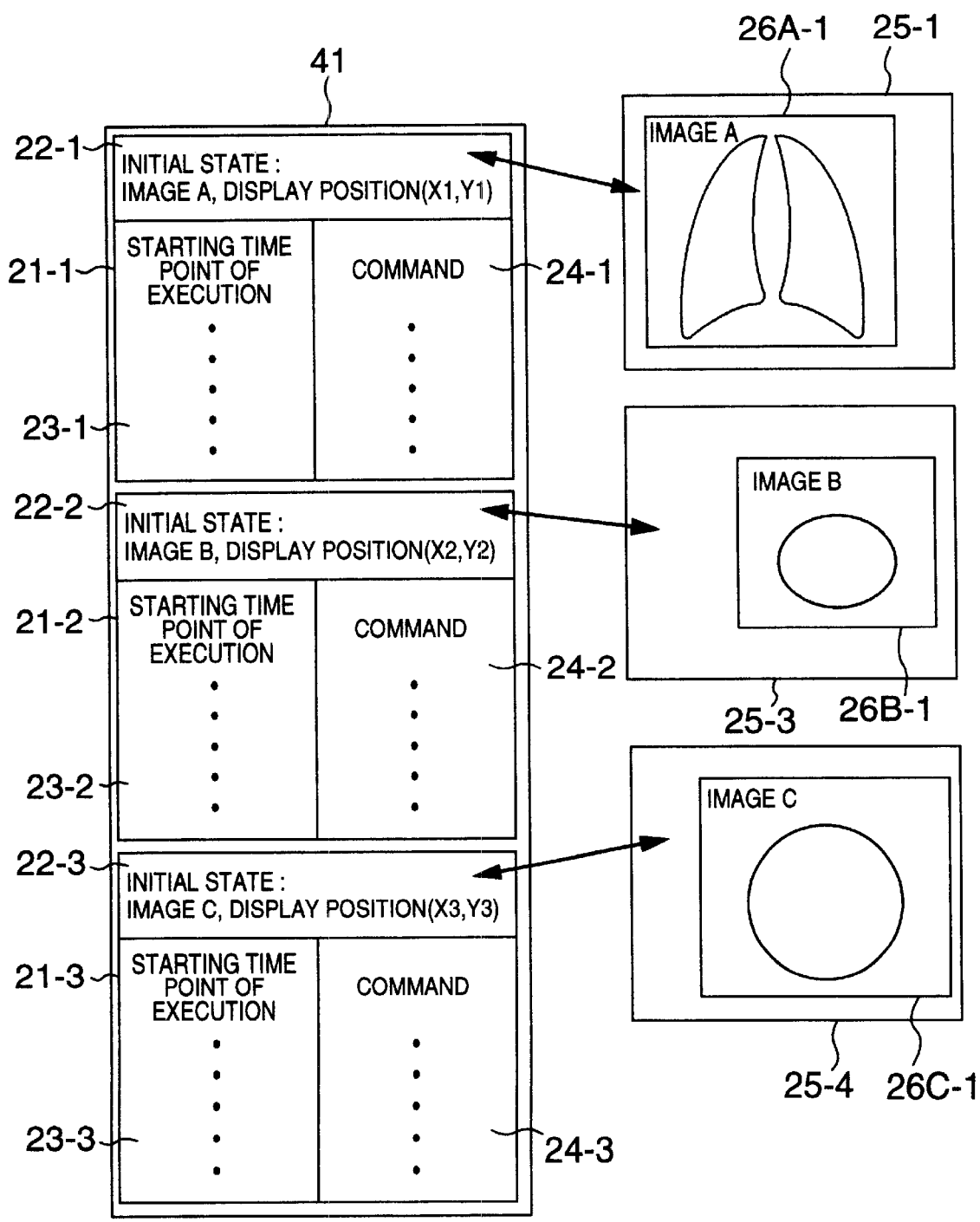
FIG. 4 illustrates structures of data blocks recorded by the method of FIG. 3a, and initial states of displayed images for the respective data blocks.

FIG. 4 shows the structure of a data block unit which is recorded according to the flow chart of FIG. 3*a* and which has a plurality of data blocks, each containing annotation command data with execution start times and an initial state. FIG. 4 also illustrates example images displayed. A data block unit 41 has three data blocks 21-1, 21-2, 21-3, which are reproduced in that order according to a procedure shown in FIG. 3*b*. That is, an image A (26) is first displayed on the computer screen 25-1, followed by an image B (26B-1) on the screen 25-3 and by an image C (26C-1) on the screen 25-4.

In a more concrete situation, when asking questions about two or more images, the questions may be recorded a number of times. In this case, the questions are recorded by repetitively performing a process of displaying a to-be-annotated image and then recording the annotations. To ask a first question, a screen 25-1 showing a desired image 26A-1 is displayed. When the recording is started, the recording step 1-2 records an initial state 22-1 of an image 26A-1 displayed on the screen 25-1 and then records commands 24-1 along with execution start times 23-1. The recorded initial state 22-1, execution start times 23-1 and commands 24-1 are combined to generate a data block 21-1. Next, the display of the image 26A-1 is terminated, and an image 26B-1 is displayed on the screen and preparations are made for the second question. When the recording is started (step 31), the recording step 1-2 records a screen 25-3 showing an initial state 22-2 of the next to-be-annotated image 26B-1 and then records commands 24-2 along with execution start times 23-2. The recorded initial state 22-2, execution start times 23-2 and commands 24-2 are combined to generate a data block 21-2. When the recording is finished, because there is the first data block that is already recorded (step 32), an addition step 33-1 adds the data block 21-2 associated with the second question at the end of the data block 21-1 associated with the first question. Similarly, for a third question, the operator terminates the display of the image 26B-1 and displays the next image 26C-1 on the screen, and then starts recording (step 31). The recording step 1-2 records a screen 25-4 showing an initial state 22-3 of the next to-be-annotated image 26C-1 and then records commands 24-3 along with the execution start times 23-3. The recorded initial state 22-3, execution start times 23-3 and commands 24-3 are combined to generate a data block 21-3. The third data block 21-3 is added at the end of the second data block 21-2 by the addition step 33-1, thus forming a data block unit 41 having these three data blocks. The positions on the recording medium of the recording areas of these data blocks are physically or logically correlated with one another to produce one data block unit.

When the data block unit 41 is reproduced, the first data block 21-1 is first reproduced at a reproducing step 6-2 to reproduce the initial state 25-1 and then the commands 24-1. After all the commands 24-1 in the data block 21-1 have been executed, the reproducing step 6-2 is ended and a check is made to see whether there is another data block (step 38). Because there is the second data block 21-2, it is designated (step 39) and reproduced by the reproducing step 6-2. The reproducing step 6-2 uses the initial state 22-2 to display the screen 25-3. All the commands 24-2 of the data block 21-2 are then executed, after which the reproducing step 6-2 is ended.

Likewise, the third data block 21-3 is reproduced at the reproduction step 6-2. The reproduction step 6-2 reproduces the initial state 22-3 of the third data block 21-3 to display the screen 25-4 and then reproduces the commands 24-3. After all the commands in the third data block 21-3 have been executed, the reproduction step 6-2 is ended. Because there is no subsequent data block, the reproduction process is terminated.

When recording is performed a plurality of times by changing the display image, the initial states of the respective to-be-annotated images which are present at the start of recording are first recorded, followed by the recording of commands along with their corresponding execution start times. For reproduction, the initial states are reproduced, followed by the commands being executed. This process of recording and reproduction ensures that even when the recording was carried out a number of times to record two or more images, these images can be reproduced accurately as they were recorded because of the recording and reproduction of the initial states.

Next, the process of editing, such as inserting or deleting commands in the form of a data block to and from the annotation command data, will be described. An operator who has referenced a data block containing a recorded question records his or her answer to that question and returns it to the questioner. At this time, the operator inserts his answers, or deletes unnecessary portions, immediately following the corresponding questions to generate answer data. First, the process of inserting commands will be explained.

FIG. 5 is a flow chart showing one example process of inserting a new data block in an original data block. A reproducing step 6-3 reproduces the original data block to a point of insertion when it stops the reproduction. A dividing step 52-1 divides the original data block at the halt point into former and latter data blocks. A recording step 1-3 records the new data block to be inserted on the recording medium, and an addition step 33-2 adds it at the end of the former data block. Further, an addition step 33-3 adds the latter data block at the end of the inserted new data.

FIG. 6 illustrates structures of data blocks when the new data block is inserted according to the flow chart of FIG. 5, and also shows example display images. In FIG. 6, reference number 21-1 represents the original data block before editing (similar to the data block 21-1 shown in FIG. 2); 21-1F and 21-1L represent first and second halves of the original data block 21-1; 21-6 represents a new data block to be inserted; 25-1 represents a screen showing the initial state of the unedited original data block; 25-2 represents a screen showing the state after all the command data in the unedited original data block have been executed; 25-5 represents a screen showing the state after the command data 24-1F in the former data block 21-1F from the unedited original data block have been executed; and 25-6 represents a screen showing the state after the command data 24-6 in the new data block 21-6 to be inserted has been executed.

The insertion process 51 reproduces the original data block 21-1 at the reproducing step 6-3 until a point for insertion is reached, at which time it stops reproduction. At this time, on the screen a line-a (27) is added and a pointer-a (28) is added and moved twice. As the result of the above steps, the screen assumes the state as shown in the screen 25-5. Next, the dividing step 52-1 divides the original data block 21-1 into the former data block 21-1F, which includes the initial state 22-1F, execution start times 23-1F and command data 24-1F, and the latter data block 21-1L, which includes the initial state 22-1L, execution start times 23-1L and command data 24-1L, and records the former and latter data blocks on a record medium. The execution start time 23-1L in the latter data block 21-1L is adjusted by using elapsed time from a point of time which it stops reproduction. In FIG. 6, it is assumed that the reproduction was stopped at 50 seconds. Thus, the execution start time of the command "ADD Text-a" in the latter data block 21-1L is adjusted to 30 seconds which is the result of subtraction the 50 seconds from the execution start time of the command "ADD Text-a" in the original data block 21-1, 80 seconds. At this time, the screen 25-5 obtained when the reproduction is halted is taken as the initial state 22-1L of the latter data block 21-1L. Next, the recording step 1-3 records the new data block 21-6 to be inserted. The screen at this time is the one 25-5 produced when the original data block 21-1 is stopped partway, i.e., the screen made by reproducing the former data block 21-1F, and therefore is taken as the initial state 22-6 of the new data block 21-6 to be inserted. The operator manipulates the screen 25-5 to add thereto line-b (61), whereby command "ADD Line b" is recorded in area 24-6 and starting time point of execution "20" is recorded in area 23-6. Thus, the recording of the inserted data block 21-6 which includes the initial state 22-6, execution start time 23-6 and command data 24-6 is terminated. The execution start time 23-1L in the latter data block 21-1L is adjusted by taking the insertion of the command data 24-6 of the inserted data block 21-6 into account. For example, the execution start time may be adjusted with the time point of the division of the original data block 21-1 taken as a starting time (=0). When the recording of the new data block 21-6 is finished, the addition step 33-2 adds the new data block 21-6 at the end of the former data block 21-1F to thereby form a data block unit including the data blocks 21-1F and 21-6. The addition step 33-3 also adds the latter data block 21-1L at the end of the inserted data block 21-6 to thereby form a data block unit including the data blocks 21-1F, 21-6 and 21-1L. Thus the insertion is complete. The positions on the recording medium of the data blocks 21-1F, 21-6 and 21-1L are physically or logically correlated with one another to form one data block unit. Namely, the data blocks 21-1F, 21-6 and 21-1L may be recorded on physically successive areas on the recording medium, or they may be recorded on any individual areas on the recording medium with a table also recorded on the recording medium in which an order of arrangement of the data blocks is described for forming a data block unit, using pointers designating the data blocks.

Reproduction of the recorded data block unit proceeds in the following manner. The initial state 22-4 of the former data block 21-1F is first displayed, as shown on the screen 25-1. This is followed by the command data 24-1F of the former data block 21-1F being executed at the execution start times 23-1F to display the screen 25-5. When the reproduction of the former data block 21-1F is finished, the inserted data block 21-6 begins to be reproduced to match the display content of the screen 25-5 to what is recorded in the initial state 22-6. Because the current screen is what the initial state 22-6 represents, the display content of the screen is left unchanged and the command data 24-6 of the inserted data block 21-6 is executed to add the line-b (61) on the screen. Then, the latter data block 21-1L is reproduced to display the initial state 22-1L. Here, in order to have the screen display what is displayed on the display screen 25-5, the line-b (61) which is a difference between the current display screen 25-6 and the screen 25-5 is deleted. When the display screen 25-5 defined by the initial state 22-1L is resumed, the command data 24-1L of the latter data block 21-1L is executed to add text-a (29) on the screen to change it to the screen 25-2. The result of reproducing the latter data block 21-1L is the screen 25-2, the same as the result of reproducing the unedited original data block 21-1.

Next, a process of deleting an intermediate part of the data block will be explained. FIG. 7 is a flow chart showing an example process for deleting commands in a data block that are supposed to be executed in a specified time duration. A dividing step 52-2 divides the data block at the time of the beginning of the intermediate part to be deleted. Further, a dividing step 52-3 divides the data block at the time of the end of the intermediate part to be deleted. In the end, the data block is divided into three blocks. A deleting step 72 removes the middle data block.

Figure 8:
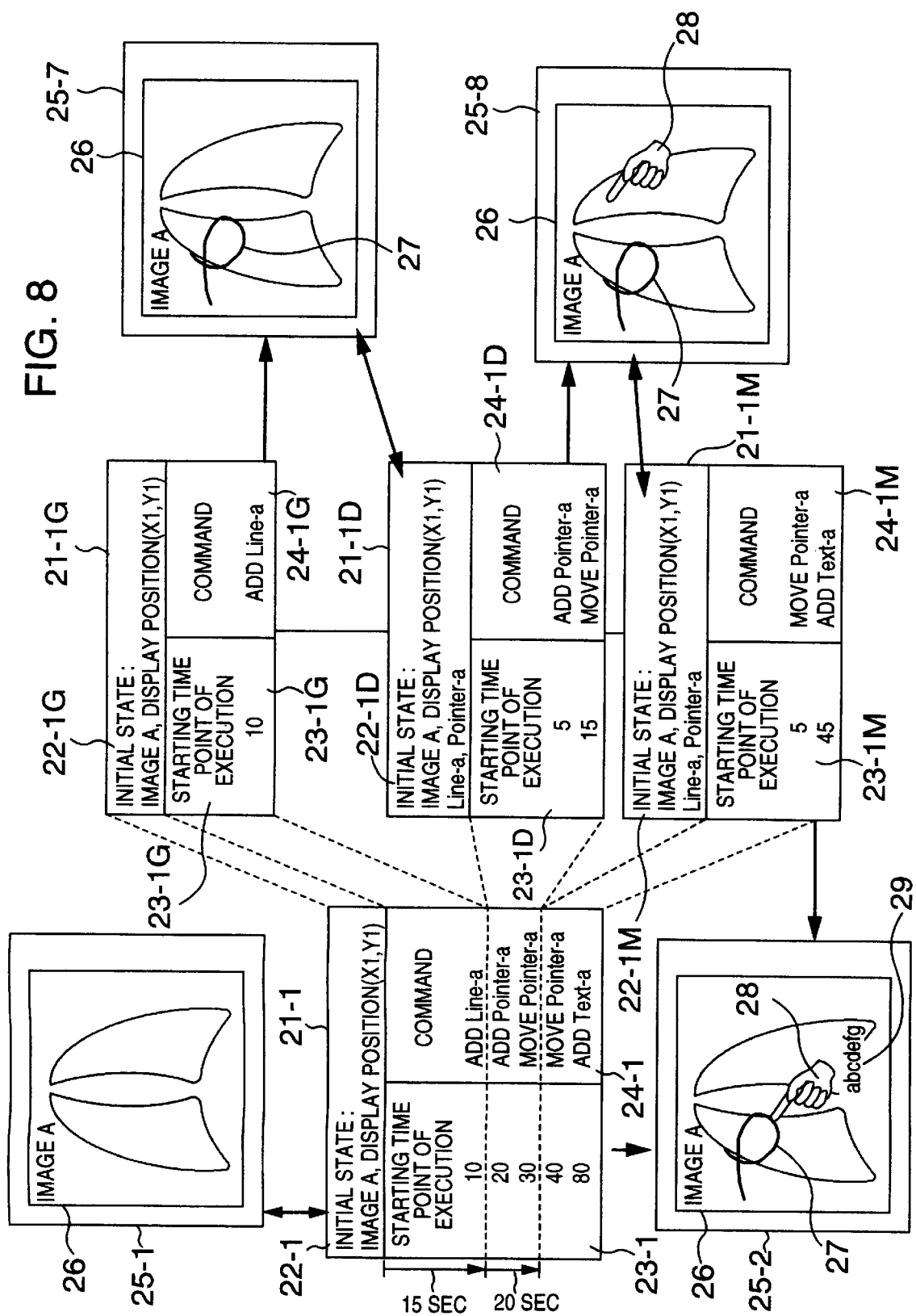
FIG. 8 illustrates how a data block structure changes when an intermediate part of the data block is deleted by using the method of FIG. 7, and also illustrates images associated with some data blocks.

FIG. 8 illustrates how the data block structure will change when an intermediate part of the command data in the original data block is deleted according to the flow chart of FIG. 7, as well as example display images. In FIG. 8, 21-1 represents an original data block before editing (similar to the data block 21-1 shown in FIG. 2); 21-1G, 21-1D and 21-1M represent a former data block, an intermediate data block and a latter data block, respectively, produced by dividing the original data block 21-1; 25-1 and 25-2 represent, respectively, a screen showing an initial state of the unedited original data block 21-1 and a screen showing a state obtained after all the commands of the original data block have been executed; 25-7 and 25-8 represent, respectively, a screen produced by reproducing the former data block 21-1G of the original data block 21-1 and a screen produced by reproducing the intermediate data block 21-1D. The intermediate data block 21-1D is the one to be deleted.

Removing a part of the command data 24-1 in the original data block 21-1 involves the following steps. First, the dividing step 52-2 divides the original data block 21-1 into a former data block and a temporary data block at the time of the beginning of the intermediate data block to be deleted. The execution start time in the temporary data block is adjusted by using elapsed time from a point in time of the beginning of the intermediate data block i.e. 15 seconds in FIG. 8. The dividing step 52-3 divides the temporary data block into two subdivided data blocks at the time of the end of the intermediate data block to be deleted. The execution start time in the latter subdivided data block is adjusted by using elapsed time from a point in time of the end of the intermediate part, i.e. 20 seconds in FIG. 8. As a result, the former data block 21-1G, the intermediate data block 21-1D and the latter data block 21-1M are formed from the original data block 21-1. At this time, the initial state 22-1G of the former data block 21-1G is the same as the initial state of the unedited original data block 21-1, as shown in the screen 25-1. The initial state 22-1D of the intermediate data block 21-1D is the state shown in the screen 25-7 which is obtained by reproducing the former data block 21-1G, i.e., by executing the command 24-1G of the former data block 21-1G in this case. The initial state 22-1M of the latter data block 21-1M is the state shown in the screen 25-8 which is obtained by reproducing the intermediate data block 21-1D. The deleting step 72 then removes the intermediate data block 21-1D. The execution start times 23-1M of the latter data block 21-1M are adjusted by taking the deletion of the commands 24-1D of the intermediate data block 23-1D into account. Even when the intermediate data block 21-1D is removed in this way, because the initial screen 25-8 to be displayed at the start of reproduction has been recorded in the subsequent data block 21-1M, the result of execution of the last data block 21-1M will be the same as the screen 25-2 which is obtained after executing the unedited original data block 21-1. The former data block 21-1G and the latter data block 21-1M that form a data block unit are recorded in the physically or logically correlated recording areas on the recording medium.

Because the intermediate data block 21-1D has been deleted, the command no longer exists for displaying the pointer-a (28), the very object to be moved by the pointer-a (28) moving command in the command data 24-1M of the latter data block 21-1M. However, the initial state 22-1M of the latter data block 21-1M includes the pointer-a (28) and thus the pointer-a (28) moving command can be executed without a conflict.

Even when the sequence of commands in the original data block is changed by insertion or deletion of annotation commands, the result of execution of any command after editing can be made equal to the result of execution of the same command before editing because the state immediately before the inserted or deleted commands are executed is saved as an unedited initial state (a state prior to insertion/deletion). Also when annotation commands are deleted, because annotations necessary for the initial state are recorded, it is possible to prevent inconsistencies in which annotations (pointer, line, etc.), the objects to be handled by subsequent commands, do not exist.

In the embodiment explained with reference to FIG. 6, for reproduction of the latter data block 22-1L after the reproduction of the new data block 21-6, a difference between the current display state of the screen 25-6 and the initial state 25-5 of the following data block is determined as "line-b", and the "line-b" is deleted to make the current display state and the initial state concurrent with each other. However, the current state may first be deleted or erased so that the initial state is thereafter generated. With this method the initial state can be reproduced easily.

In the embodiment of FIG. 6, even when the initial state 22-6 of the newly inserted data block 21-6 is the same as the result 25-5 of execution of the former data block 21-1F, the content of the execution result of the former data block is recorded. It is also possible to record in the initial state 22-6 a message indicating that the initial state 22-6 is the same as the result of execution of the former data block 21-1F. This method can reduce the amount of data recorded. Further, although in the embodiment shown in FIG. 6 the original data block 21-1 is reproduced partway and divided for the new data block 21-6 to be inserted, it is also possible to specify a particular time in the original data block, divide the original data block and insert the data block there. This method enables insertion of a data block at a specified time without performing reproduction.

In the embodiment explained by referring to FIGS. 7 and 8, a method of deleting an intermediate part of the command data in the original data block has been described. When a part of the original data block is to be deleted which ranges from the start of the command data to an intermediate location or from an intermediate location to the end of the command data, the dividing step of FIG. 7 needs only to be performed once. The original data block is divided at the execution start time of the last or first command of the command group to be deleted and the former data block or latter data block is removed. By combining these methods, one or more commands with arbitrary execution start times can be eliminated from the original data block. It is also possible to perform editing such as changing the order of data blocks. Data blocks generated during the course of editing have their own initial states, so that the recorded contents can be reproduced correctly even when the order of these data blocks is changed.

In the explanation of the insertion process in FIG. 6 and the deletion process in FIG. 8, it has been described that a screen obtained by executing a post-edit command is made to match a screen obtained by executing the same unedited command. It is possible to reflect the result of editing on the reproduction performed after the point of editing. For example, in the case of FIG. 6, if the data block is reproduced to the last, the result of execution of a new data block inserted at an intermediate location disappears from view. It is possible to show the result of the inserted data block and the unedited result at the same time so that they can be viewed overlapping each other. In that case, an initial state is newly generated when inserting the new data block.

Figure 9:
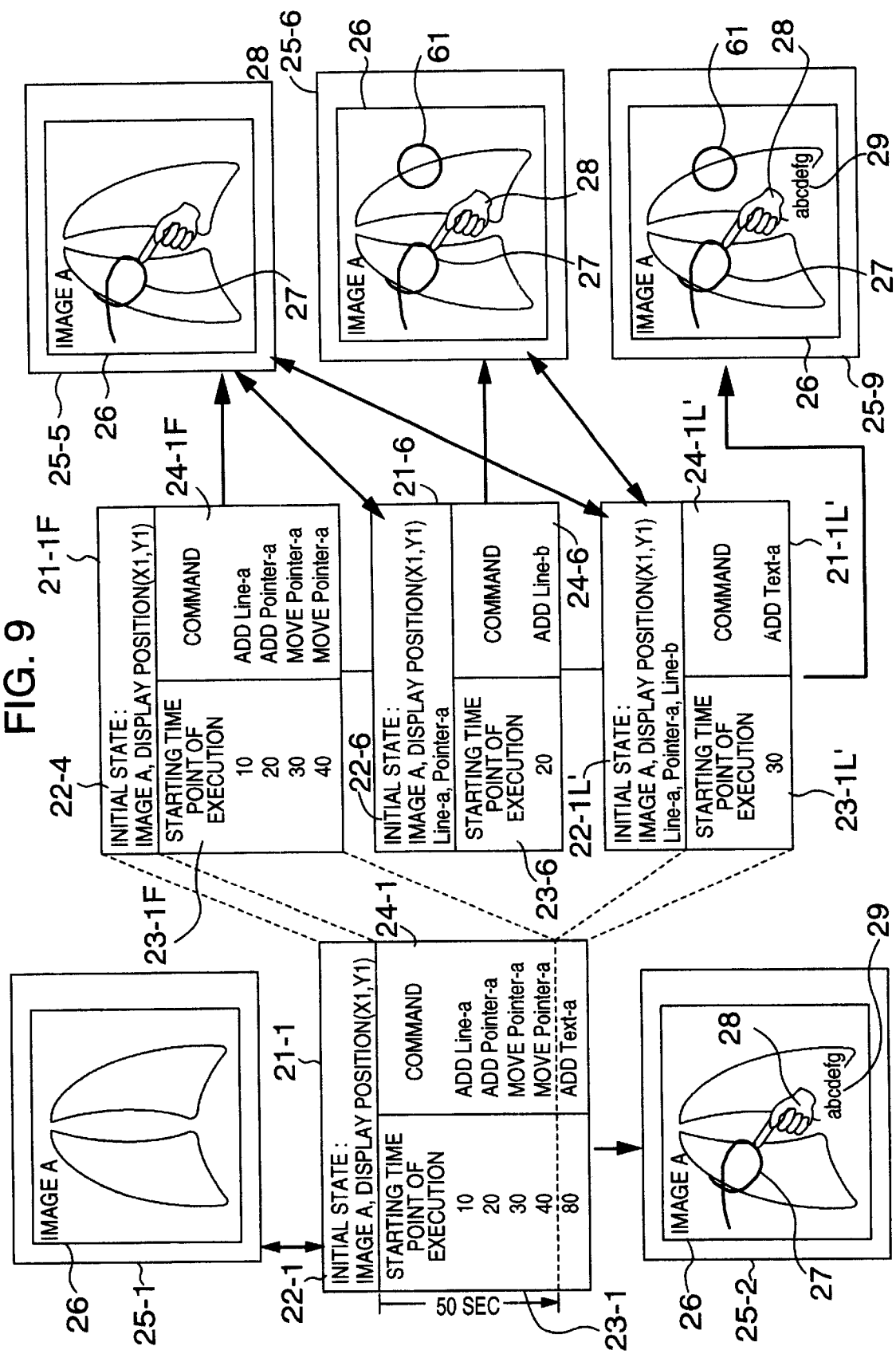
FIG. 9 illustrates how a data block structure changes when an initial state that reflects the result of execution of an inserted data block is newly generated by an annotation command data editing method, and also illustrates images associated with some data blocks, according to one embodiment of the invention.

FIG. 9 shows how a data block structure changes when an initial state is newly generated during the process of inserting a new data block, and also shows example display images. When, according to the procedure shown in FIG. 5, the insertion process has proceeded to the reproducing step 6-3 (i.e., when the reproduction is stopped at a point at which to insert commands), the state shown in the screen 25-5 is obtained. The dividing step 52-1 divides the original data block 21-1 into a former data block 21-1F and a temporary latter data block 21-1L'. At this time the initial state of the temporary latter data block is the same as in the case of FIG. 6 shown on the screen 25-5. The new data block 21-6 to be inserted is recorded, the addition step 33-2 adds the new data block 21-6 at the end of the former data block 21-1F, and the addition step 33-3 adds the latter data block 21-1L' at the end of the new data block 21-6. The latter data block 21-1L' is the same as the temporary latter data block except for the initial state, and its initial state 22-1L' is newly generated.

Here, in order that when the reproduction of all the data blocks is complete, the result of executing the command of the inserted new data block 21-6, or the annotation line-b (61), can also be viewed, the following steps are taken. That is, comparison is made between the screen 25-5 representing the original initial state, i.e., the state generated after the former data block 21-1F has been reproduced, and the screen 25-6 representing the state obtained by executing the command 24-6 of the inserted new data block 21-6. If there is any difference, the initial state of the data block 21-1L' is replaced with the screen 25-6 and the latter data block is generated. The execution start time 23-1L' of the latter data block 22-1L' is adjusted by considering the insertion of the command 24-6 of the inserted data block 21-6. The data blocks 21-1F, 21-6 and 21-1L' that form one data block unit are recorded in physically or logically correlated recording areas on the recording medium. Reproducing this data block unit produces the following screens. The data block 21-1L', when reproduced to the end, displays the screen 25-9 that shows the annotation line-b (61) produced by the command 24-6 of the inserted new data block 21-6 and the text-a produced by the command 24-1L' of the latter data block 21-1L' so that one can see them at the same time on the screen.

As in the example of FIG. 9, a synthesized state produced by combining the result of executing the inserted processing with the unedited data can be shown to a viewer. With this method, when the screen is to be printed out after the data has been reproduced to the end, it is possible to print out a screen that shows a combined result of the unedited processing and the inserted processing.

Although no problem occurred when the initial state of the latter data block 21-1L' was replaced with a state that was obtained by reproducing the inserted data block 21-6 in the case of FIG. 9, a command of the latter data block 21-1L' may conflict with a command of the inserted data block 21-6, depending on the content of a command of the inserted data block. For example, when the command data 24-6 of the inserted data block 21-6 includes a command for terminating the display of the image A, a command in the data block 21-1L' for adding the text-a cannot be executed because any image to be annotated does not exist. To prevent such inconsistencies, the initial state of the latter data block is replaced by another. However, such replacement may be prohibited, for example, when it is proved that no image to be annotated by commands in the command data 24-1L' of the latter data block 21-1L' is included in a new initial state to be substituted for the initial state of the latter data block 21-1L', as a result of comparison between an image to be annotated by the command in the command data 24-1L' and the new initial state to be substituted. Furthermore, it may be prohibited to include, in the command data 24-6 of the insertion data block 21-6, a command. to terminate display of an image to be annotated by the original data block 21-1, a command to delete or erase a pointer or a line or a character dealt with by the original data block 21-1, or the like. By these measures, it is possible to ensure that a to-be-annotated object exists when commands in edited annotation command data are executed. In addition, when an edited data block is reproduced, any command for which no to-be-annotated object exists may be skipped. Thereby, it is possible to lessen limitations on the data block editing.

In the example of FIG. 9, although the initial state of the latter data block is generated at time of editing based on the result of comparison between the result of execution of commands of the former data block and the result of execution of the inserted new data block, it is also possible to generate a new initial state at time of reproduction based on the result of comparison between the result of execution of commands of the former data block and the initial state of the insertion data block which is about to be reproduced. For example, when reproducing the latter data block 21-1L of FIG. 6 in accordance with the reproducing process shown in FIG. 3b, an initial state corresponding to the screen 25-6 shown in FIG. 9 may be generated and reflected on the screen, instead of using the initial state screen 25-1L, and then the command data 24-1L' of the latter data block 21-1L' may be reproduced. This method allows the user to select, at time of reproduction, between reproducing the original state and leaving the result of processing added by editing.

Figure 10:
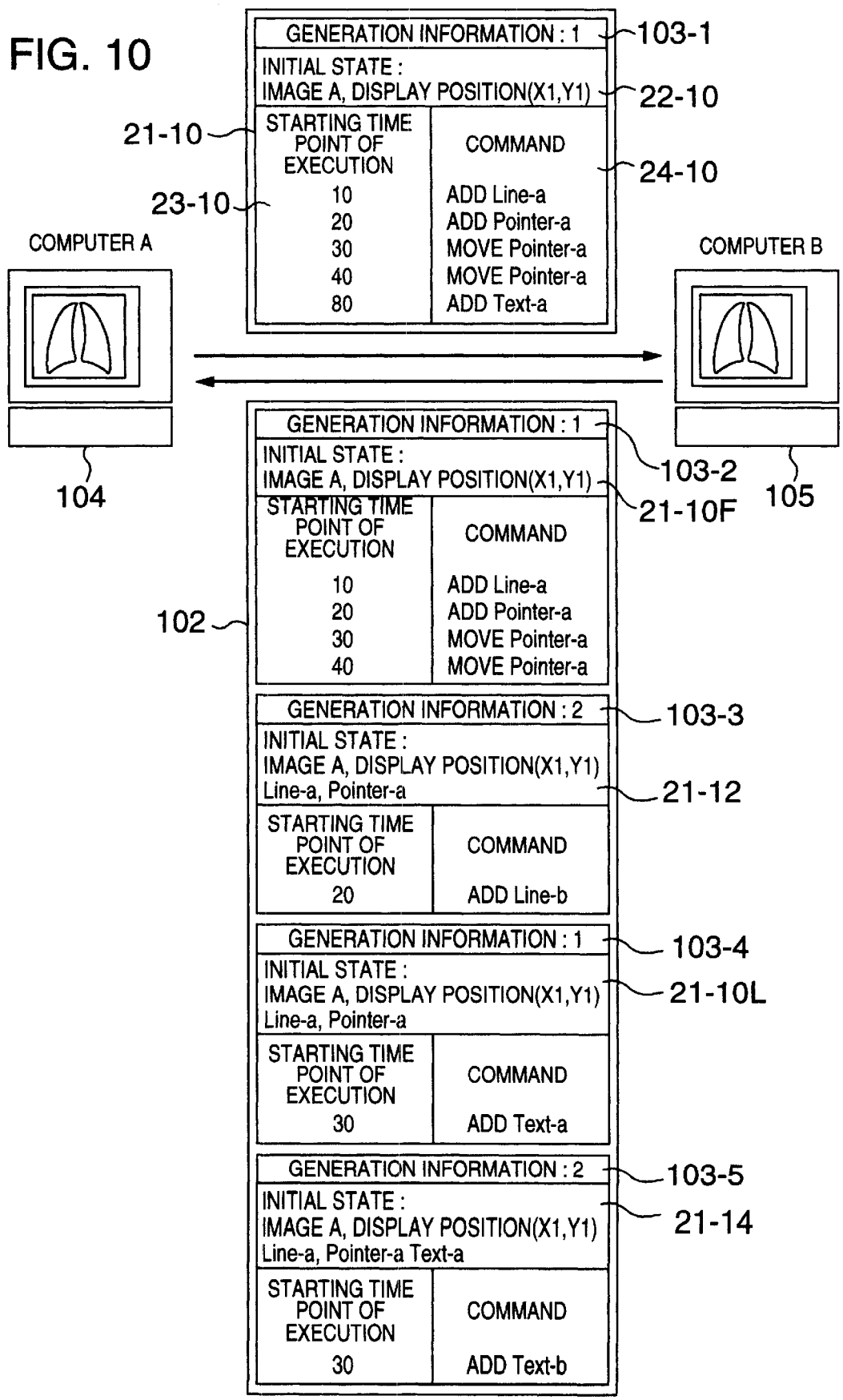
FIG. 10 illustrates how annotation command data having data blocks containing attributes, such as generation information, is transmitted and received, according to one embodiment of the invention.

Next, a method of adding attributes such as generation information to each data block according to a data block recording stage (or phase) and reproducing the data blocks by using the generation information. FIG. 10 shows one example case where data blocks containing generation information are transferred between two computer terminals. The generation information refers to data that indicates when, where and how the associated data block was generated. Here, in a data block unit including a plurality of data blocks, those data blocks that were recorded when the annotation command data was newly generated are assigned with generation information of 1. Those data blocks that were added by subsequent editing are given generation information of 2, 3 and so on in an ascending order, thus distinguishing the phases when the data blocks were generated.

In FIG. 10, messages including data blocks or a data block unit are transferred between operators at computer terminals 104, 105. A data block 21-10 contained in a message transmitted from the computer terminal A (104) has generation information 103-1. A data block unit 102 contained in a message, which was generated by editing the received message data block 21-10 and was sent back by an operator at the computer terminal B (105), has data blocks 21-10F, 21-12, 21-10L, 21-14 assigned with generation information 103-2, 103-3, 103-4, 103-5, respectively.

The computer terminal A records a question about the image A and generates a message containing the data block 21-10. At this time, generation information 103-1 is added to the data block 21-10. The generation information 103-1, initial state 22-10, execution start time 23-10 and command data 24-10 in the data block 21-10 are correlated with one another in their arrangement on a communication medium. The data block 21-10 is newly generated by the computer terminal A and thus its generation information is 1. The computer terminal A sends the message containing the data block 21-10 to the computer terminal B. The operator at the computer terminal B reproduces the data block 21-10 contained in the received message. To answer the question that is displayed as a result of executing a command "add text-a" in the data block 21-10, a data block unit 102 is generated by inserting a data block 21-12 into the data block 21-10 and adding a data block 21-14. At this time, the generation information 103-2, 103-4 of former and latter data blocks 21-10F, 21-10L, which were generated by dividing the original data block, are the same as that of the original data block, i.e., 1. The generation information of the inserted new data blocks 21-12, 21-14 are 2. Then, the computer terminal B returns a message containing a data block unit 102 to the computer terminal A. The data blocks 21-10F, 21-12, 21-10L, 21-14 in the data block unit 102 are, at time of transmission, correlated with one another in their arrangement on the communication medium. At the computer terminal A that has received the message containing the data block unit 102, the operator reproduces the data block unit 102 and references the answer that is displayed as a result of executing commands "add line-b" and "add text-b" in the inserted data blocks 21-12, 21-14. The operator at the computer terminal A, when he decides that it is not necessary to view his own question, can reproduce only the inserted data block 21-12, 21-14 with generation information of 2 and thus see only the answer to his question.

As in the example shown in FIG. 10, the provision of generation information allows the operator to know in what phase the data blocks were recorded, manage them according to the generation information, and reproduce the data block by selecting desired generation information, which in turn makes it possible to reference only answers to queries, shortening the time for referencing.

Although, in the example of FIG. 10, only one generation is selected for reproduction, a plurality of generations may be selected. In this example, the generation information is added according to the phase when the data block was recorded. The generation information or attributes may be generated from information such as name and ID of an operator who has performed recording and from particular information recorded such as facility and equipment. The name of an operator may also be recorded like generation information, and a desired data block may be selected by designating the associated operator name and then reproduced. This method allows the user to select data blocks by identifying a recording source, to display the name of a recorder who recorded the data blocks during reproduction, and to display data blocks in different colors for different operators. For the transmission and reception of messages, use may be made of a technique disclosed in a paper entitled "Synchronized Voice and Image Annotation and Remote Consultation and Diagnosis for the Global PACS" (Proc. SPLE, vol. 2165, pp. 9–20 (1994)).

Figure 11A:
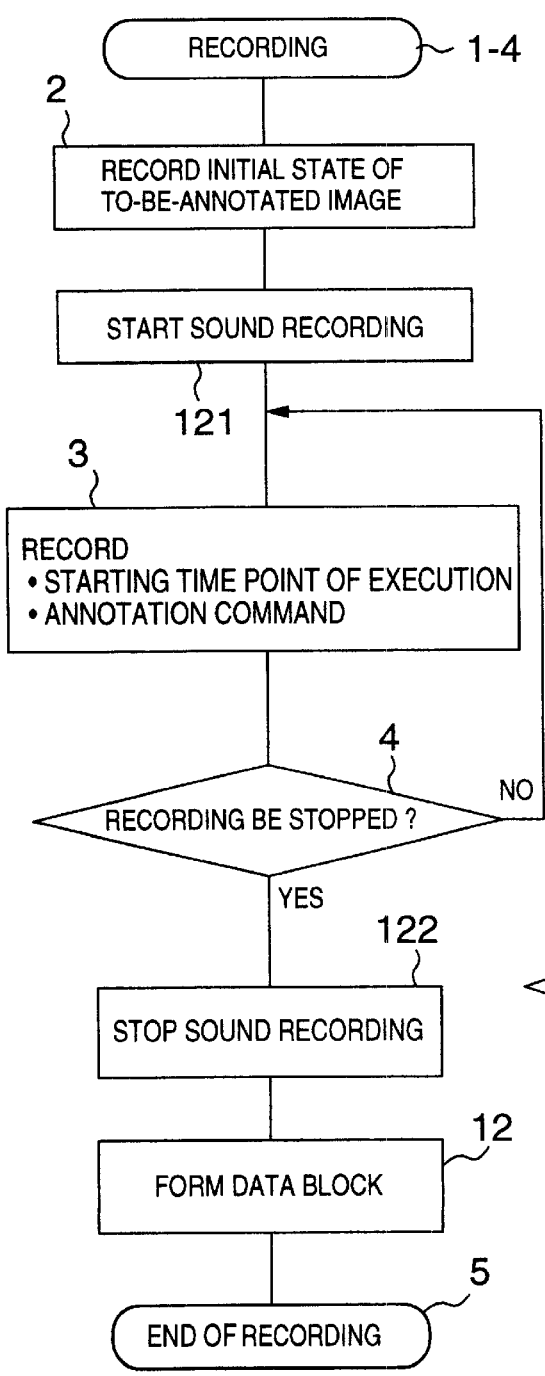
FIGS. 11a and 11b are flow charts showing methods for recording and reproducing multimedia data which includes sound data in addition to the annotation command data shown in FIGS. 1a and 1b.
Figure 11B:
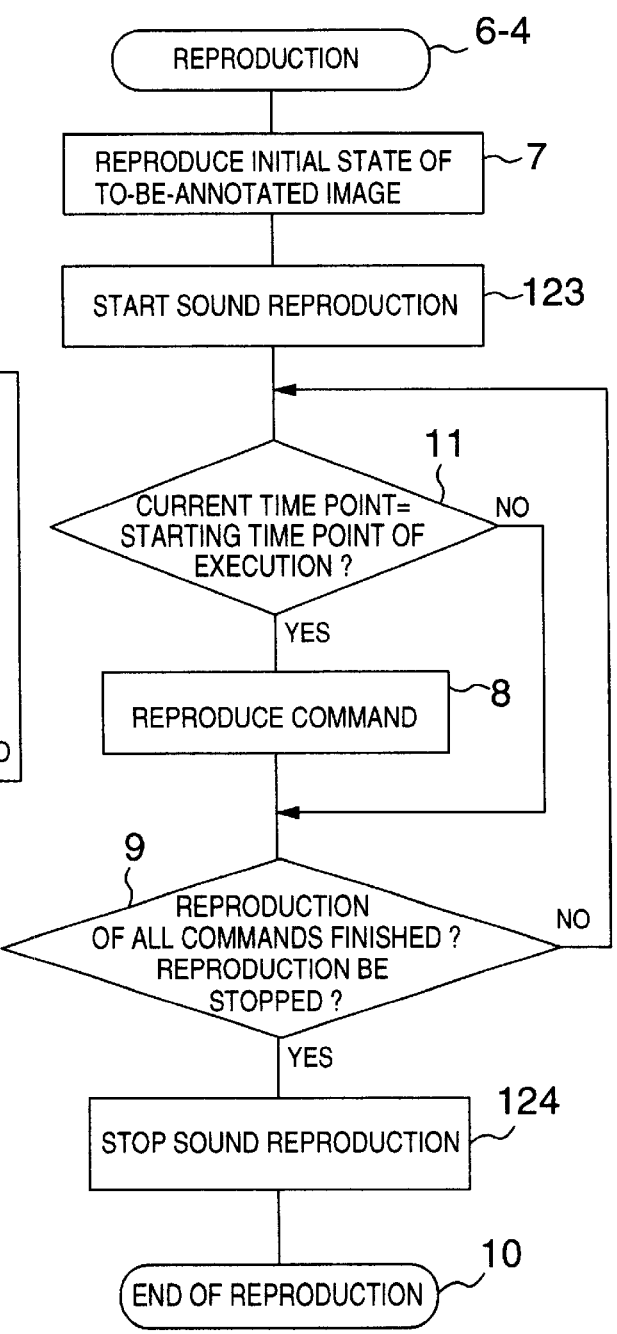

FIGS. 11a and 11b represent example cases for handling multimedia data, in which the functions of recording/reproducing sound data such as voice are added to the processes for recording/reproducing command data as shown in FIGS. 1a and 1b. FIG. 11a is a flow chart for the recording process and FIG. 11b a flow chart for the reproducing process. A recording process 1-4 starts recording sound data such as voice data at a sound recording start step 121 and stops recording sound data at a sound recording stop step 122. A reproduction process 6-4 starts reproducing sound data such as voice data at a sound reproduction start step 123 and stops reproducing sound data at a sound reproduction stop step 124. Other steps are the same as the corresponding steps in FIGS. 1a and 1b.

Next, we will explain about an example case of handling multimedia data, in which command data is recorded/reproduced in synchronization with sound data and/or motion picture data. FIGS. 12a to 12c are diagrams showing example data block structures each having a combination of sound data or motion picture data and command data. FIG. 12a shows an example of a data block 111 having a combination of an initial state, command data with execution start times, and sound data 114-1. FIG. 12b shows an example of a data block 112 having a combination of an initial state, command data with execution start times, and motion picture data 115-1. FIG. 12c shows an example of a data block 113 having a combination of an initial state, command data with execution start times, sound data 114-2, and motion picture data 115-2.

In recording multimedia data containing a combination of command data and sound data, when the recording process 1-4 shown in FIG. 11a is started, an initial state recording step 2 records an initial state and a sound recording start step 121 starts recording sound data before starting to record commands. When the recording of execution start times and commands is stopped (step 4), a sound recording stop step 122 stops recording sound data. With the above steps performed, a data block 111, which includes the initial state, the recorded command data with execution start times, and the sound data 114-1, is generated.

In reproducing the data block 111, the reproduction process 6-4 shown in FIG. 11b reproduces the initial state (step 7), starts reproducing the sound data 114-1 at the sound reproduction start step 123, starts a timer and, when the elapsed time of the timer reaches the execution start times (step 11), reproduces the corresponding commands (step 8). When all the commands have been reproduced or the reproduction is stopped (step 9), a sound reproduction stop step 124 stops reproducing the sound data.

While FIGS. 11a, 11b and 12a have shown a method of recording and reproducing the command data with execution start times and the sound data in synchronization with each other, motion picture data rather than sound data may be used in the recording and reproduction of the data block 112 as shown in FIG. 12b. Further, it is possible to record sound data and motion picture data simultaneously and reproduce the data block 113 as shown in FIG. 12c.

These methods described by referring to FIGS. 11a and 11b and FIGS. 12a to 12c allow recording and reproduction of multimedia data blocks that are annotated using a combination of sound, such as voice, and motion picture. Recording and reproducing command data in combination with sound and motion picture can make queries and answers more understandable during a remote consultation session. When performing editing, such as insertion and deletion, on a data block consisting of commands and sound and/or motion picture data as shown in FIGS. 12a to 12c, the data block needs to be divided. In this case, a dividing step (52-1 in FIG. 5, 52-2 and 52-3 in FIG. 7) divides sound and/or motion picture data at the same point of time that the command data is divided. The command and the sound and/or motion picture recorded at the same point of time are combined in one and the same data block. With this method it is possible to divide a data block including a combination of command data and sound and/or motion picture data and perform editing such as insertion and deletion.

When recording a plurality of data blocks which include sound and/or motion picture data in addition to the initial state, they may be of various kinds, such as a data block including command data with execution start times and sound data, one including command data with execution start times and motion picture data, one including command data with execution start times and sound and motion picture data, and one including only command data with execution start times. This method makes it possible to select a kind of data to be recorded, as required, at time of recording.

While this embodiment uses as the command execution start time the time which elapses from when the commands of a data block begin to be recorded, it is possible to use an absolute time or a time difference from the previous command. The use of the absolute time can reduce the processing of time calculation and simplify the recording process because there is no need to calculate. The adjustment of the execution start time during the dividing step can be made unnecessary by using the time difference from the previous command.

Next, as an example of a system which applies to the medical field the method of editing command data attached with execution start times, we will explain about a system that records in multimedia data blocks queries and answers regarding a medical image to support consultation and diagnosis sessions between doctors at remote places. FIG. 13 shows an example system that supports medical examinations by using multimedia data blocks that contain a combination of command data with execution start times and voice and motion picture data. The system body 131 is a computer, such as personal computer and workstation, which has a monitor 132 for displaying medical information and motion picture.

The system has a command controller 133 for controlling command data and a voice/motion picture data controller 134 for controlling voice and motion picture data. The data controller 134 also includes a medium recording/reproduction device. The command controller 133 displays on the monitor 132 a control panel 145 for inputting commands for recording and reproduction. When an operator operates a replay button 146, a record button 147 and a stop button 148, the command controller 133 starts or stops the recording and reproduction of multimedia data. During recording, the command controller 133 records commands generated from input devices such as mouse 136 and keyboard 137. During reproduction, the command controller 133 reproduces the recorded commands and displays a medical image 138 on the screen, moving a pointer 139 indicating a reference portion on the medical image 138 and displaying a line 140. The voice/motion picture data controller 134 is controlled by the command controller 133 to record in a recording medium voice entered from a microphone 141 and motion picture entered from a camera 142. During reproduction, the voice/motion picture data controller 134 outputs voice to a speaker 143 and displays motion picture 144 on the monitor 132. The command controller 133 executes a recording process 1-4, a reproduction process 6-4, an insertion process 51, and a deletion process 71. The voice/motion picture data controller 134 receives control signals for starting and stopping the recording and reproduction (121, 122, 123, 124) from the command controller 133 and records and reproduces voice and motion picture accordingly.

Commands used in this embodiment include such operation commands as displaying and moving a pointer specifying a particular part on the image being referenced and displaying lines and characters on the image, as well as image processing commands including enlargement and reduction of the image, changing the tone of the image, and filtering.

A system shown in FIG. 13 is installed in a plurality of medical facilities, such as hospitals, clinics and so on, so that information can be exchanged between the facilities. These facilities are interconnected via network and the contents recorded on a recording medium are transferred to the other site in the form of e-mail. For example, a physician in a clinic and a specialist in a hospital are interconnected, and the physician can put questions about a medical image taken at the clinic to the specialist. The specialist at the hospital returns his answer to the question to the referring physician. Because multimedia data is used for preparing queries and answers, they can be prepared in a manner convenient and understandable to doctors concerned. Medical images are produced in large quantities in one examination and the clinic side may have a plurality of questions concerning a plurality of images. Because a specialist at a hospital is busy, the referring clinic side prepares and records a short-duration question and repeats this process by changing the image so that the specialist can quickly view individual questions. The hospital side repeats the process of reproducing an initial state and commands to quickly refer to a plurality of questions. The specialist makes his answer by quoting the question so that the clinic doctor can easily associate the answer with the question. When there are two or more questions, answers can be inserted immediately after the associated questions and editing such as insertion and deletion of data as described in this embodiment may be performed to generate an easily understandable reply.

The method of transmitting information by using e-mail over a communication medium has been described. Other methods for information transfer may also be used, which include a method that transfers files containing recordings over communication mediums such as a private line or a public line to a destination and a method which, without using a network, stores the recordings in a recording medium, such as floppy disk and magnetooptical disk, and transports the recorded medium. These methods can be selected according to the requirements of environment in which the system is used, such as the capacity of the network and the need for information security. Although this embodiment has described a case of information exchange between a clinic and a hospital, this system is also applicable to information exchange among a variety of medical facilities, such as inspection centers and specialized hospitals. The recorded contents can be used not only for information exchange but also as educational materials. Recording the process of diagnosis made by a specialist can provide information about on what points a specialist focuses his attention in examining the image.

While in this embodiment we have taken as an example a data structure in which command data, sound data and motion picture data are written into a data block in one area on a recording medium, other data structures can be used in which data is stored in separate areas.

FIGS. 14a and 14b show an example data structure in which entities of command data, sound data and motion picture data are stored in an arbitrary area on the recording medium and in which pointers indicating actual storage locations of the command data, sound data and motion picture data are stored in another area on the recording medium. Data blocks 151-1 to 151-3 shown in FIG. 14a include, in addition to generation information, initial state pointers (Fn: n=1, 2, 3) 152, command data pointers (Cn: n=1, 2, 3) 153, sound data pointers (Sn: n=1, 2, 3) 154, and motion picture data pointers (Mn: n=1, 2, 3) 155. Actual data (data entity) shown in FIG. 14b is stored in another area 156 of the recording medium and has a region to store the data and a region to store information representing the data storage locations. FIG. 14a shows a data block 151-2 inserted between data blocks 151-1 and 151-3. Because pointers are used, the data can be divided based on the locations specified by the pointers. The data stored in one data block is divided, for example, into C1 and C2, into S1 and S2 and into M1 and M2, by changing the pointers without changing the actual data locations. The actual data of the data block 151-2 inserted afterward is added at the end of the original data, as shown in FIG. 14b. The data blocks are reproduced in an order different from the order in which the actual data are arranged. As shown in FIGS. 14a and 14b, even when editing such as data division and insertion is performed simply by changing the pointers, not the actual data, in the data block, the order of reproduction can be altered easily without moving the actual data.

While, in the example shown in FIGS. 14a and 14b, pointers for an initial state, command data, sound data and motion picture data are stored in the data block, the data block may also have actual data stored therein in a mixed arrangement with the pointers. In this embodiment, the data blocks are arranged in the order in which they are reproduced. It is also possible to prepare a table that manages the order of data blocks and specify pointers for the data blocks. This method renders unnecessary the moving of the data blocks themselves when they are edited, thus simplifying the editing process. Although this embodiment concerns operations performed on an image displayed on a screen, this process can also be applied to the control of operation of mechanical equipment. In that case, because an initial state of the mechanical equipment and commands for executing subsequent operations on the mechanical equipment are recorded, the mechanical equipment can be made to operate according to the recorded operations during the reproduction process.

In the embodiments described above, our explanation concerns terminals having both functions of recording and reproduction. Simplified terminals with only a recording function or reproduction function may be used. For example, a terminal with only the recording function shown in FIG. 3a can be used, for example, for a doctor to record a series of image diagnosis operations as evidence.

A terminal with only the reproduction function shown in FIG. 3b can be used for educational purposes, as when the recorded diagnosis operations conducted by a medical specialist are referenced. By using such a recording-only or reproduction-only edit method, the configuration of the terminal can be simplified.

In the above-described method for editing command data attached with execution start times, because the initial state of a to-be-annotated image is recorded at the start of the recording process, the result of annotations performed prior to the start of the recording process can be recorded and reproduced efficiently. Further, because the initial state and the command data are treated as one data block, the editing of the command data can be performed easily and the original information after editing can also be reproduced correctly. Further, by transferring multimedia data, a system can be realized which enables smooth information exchange among medical facilities.

What is claimed is:

1. A method of editing annotation command data to which starting time points of execution are attached, the annotation command data being arranged according to the starting time points of execution, the method comprising the steps of:

recording as an initial state a state of a to-be-annotated image and annotations on said to-be-annotated image both existing at an initial state recording time when the recording is started;

recording command data and a starting time point of execution of the command data, wherein a data block is formed which includes the initial state and the command data with the starting time point of execution;

reproducing the initial state of the to-be-annotated image and said annotations;

reproducing the command data to execute it at the starting time points of execution to annotate the to-be-annotated image, wherein the to-be-annotated image held in the data block is annotated;

dividing said command data to which the starting time points of execution are attached in the data block into command data of a first data block and command data of a second data block; and making an initial state of the second data block identical with a state of the first data block obtained by executing all the command data of the first data block, wherein said annotation command data includes such a command that the result of execution of said command is dependent upon another command that has an earlier starting time point of execution than said command.

2. A method of editing an annotation command data recorded on a medium, said annotation command data being in the form of an original data block including a first initial state for a to-be-annotated image and a first series of annotation commands and a starting time point of execution for each of the first commands, said first initial state being representative of a state of the to-be-annotated image at a first initial state recording time when recording of the first initial state is started and including an annotation on the to-be-annotated image existing at the first initial state recording time when the first initial state recording is started, said first commands being for annotating said to-be-annotated image having the annotation existing at the first initial state recording time, the method comprising the steps of:

reproducing, on a display screen, said initial state of said to-be-annotated image having said annotation;

executing a former part of said first series of commands at their associated starting points of execution to annotate said to-be-annotated image, and reproducing, on said display screen, a sequence of changes of a displayed image caused by the execution of said former part of the first series of commands;

preparing, from said original data block, a former data block including a former initial state identical with said first initial state and a former series of commands identical with said executed former part of said first series of commands and a former starting time point of execution for each of said former series of commands identical with the starting time point of execution for each of said executed former part of said first series of commands;

preparing an insertion data block including a second initial state and a second series of annotation commands and a second starting time point of execution for each of said second series of commands, said second initial state being identical with a state in which said former part of said first series of commands have been executed;

executing said second series of commands at their associated starting points of execution of said insertion data block to annotate the displayed image in said second initial state and reproducing, on said display screen, a sequence of changes of the displayed image caused by the execution of said second series of commands;

preparing, from said original data block, a latter data block including a latter initial state and a latter series of commands identical with the remaining part of said first series of commands and a latter starting time point of execution for each of said latter series of commands; and placing said former data block, said insertion block and said latter data block on said medium, said former data block, said insertion block and said latter data block being associated in their location with each other to form a data block unit in which said insertion data block is inserted between said former and latter data blocks prepared from said original data block, said latter time point of execution being adjusted in consideration of the insertion of said insertion data block, wherein the annotation command data includes such a command that the result of execution of said command is dependent upon another command that has an earlier starting time point of execution than said command.

3. A method of editing an annotation command data recorded on a medium, said annotation command data being in the form of an original data block including a first initial state for a to-be-annotated image and a first series of annotation commands and a starting time point of execution for each of the first commands, said first initial state being representative of a state to the to-be-annotated image at a first initial state recording time when recording of the first initial state is started and including an annotation on the to-be-annotated image existing at the first initial state recording time when the first initial state recording is started, said first commands being for annotating said to-be-annotated image, the method comprising the steps of:

reproducing, on a display screen, said initial state of said to-be-annotated image having said annotation;

executing a former part of said first series of commands at their associated starting points of execution to annotate said to-be-annotated image and reproducing, on said display screen, a sequence of changes of a displayed image caused by the execution of said former part of the first series of commands;

preparing, from said original data block, a former data block including a former initial state identical with said first initial state and a former series of commands identical with said executed former part of said first series of commands and a former starting time point of execution for each of said former series of commands identical with the starting time point of execution for each of said executed former part of said first series of commands;

preparing, from said original data block, a temporary data block including a temporary initial state identical with a state in which said former part of said first series of commands have been executed and a temporary series of commands identical with the remaining part of said first series of commands and a temporary starting time point of execution for each of said temporary series of commands;

executing a former part of said temporary series of commands at said temporary starting time point of execution to annotate the displayed image in said temporary initial state and reproducing, on said display screen, a sequence of changes of the displayed image caused by the execution of said former part of the temporary series of commands;

preparing, from said original data block, an intermediate data block including an intermediate initial state identical with a state in which said former part of said temporary series of commands have been executed and an intermediate series of commands identical with said executed former part of said temporary series of commands and an intermediate starting time point of execution for each of said intermediate series of commands identical with the starting time point of execution for each of said executed former part of said temporary series of commands;

preparing, from said original data block, a latter data block including a latter initial state identical with a state in which said former part of said temporary series of commands have been executed and a latter series of commands identical with the remaining part of said temporary series of commands and a latter starting time point of execution for each of said latter series of commands; and placing said former data block and said latter data block on said medium, said former data block and said latter data block being associated in their location with each other to form a data block unit in which said intermediate data block has been deleted, said latter time point of execution being adjusted in consideration of the deletion of said intermediate data block, wherein the annotation command data includes such a command that the result of execution of said command is dependent upon another command that has an earlier starting time point of execution than said command.

* * * * *